(12) United States Patent
Leverett et al.

(10) Patent No.: US 7,364,759 B2
(45) Date of Patent: Apr. 29, 2008

(54) SKIN WHITENING COMPOSITIONS CONTAINING BLACK COHOSH EXTRACT

(75) Inventors: Jesse C. Leverett, Grand Rapids, MI (US); Stephen R. Missler, Grand Rapids, MI (US); Haeri Roh-Schmidt, Ada, MI (US); Amitabh Chandra, Grand Rapids, MI (US)

(73) Assignee: Access Business Group International LLC, Ada, MI (US)

( * ) Notice: Subject to any disclaimer, the term of this patent is extended or adjusted under 35 U.S.C. 154(b) by 267 days.

(21) Appl. No.: 10/979,344

(22) Filed: Nov. 1, 2004

(65) Prior Publication Data

US 2005/0112220 A1    May 26, 2005

Related U.S. Application Data

(62) Division of application No. 10/417,914, filed on Apr. 16, 2003, now Pat. No. 7,060,304.

(51) Int. Cl.
  *A01N 65/00* (2006.01)
  *A61K 31/74* (2006.01)
  *A61K 8/00* (2006.01)

(52) U.S. Cl. .................. 424/725; 424/773; 424/78.03; 424/62

(58) Field of Classification Search ................. 424/725, 424/773, 78.03, 401
See application file for complete search history.

(56) References Cited

U.S. PATENT DOCUMENTS

| | | | |
|---|---|---|---|
| 5,063,056 | A | 11/1991 | Yamamoto |
| 6,153,208 | A | 11/2000 | McAtee et al. |
| 6,342,254 | B1 | 1/2002 | Soudant et al. |
| 6,352,685 | B2 | 3/2002 | Hoshino et al. |
| 2001/0014311 | A1 | 8/2001 | Hoshino et al. |
| 2002/0041906 | A1 | 4/2002 | Tao |
| 2002/0054922 | A1 | 5/2002 | Lerner et al. |
| 2002/0071878 | A1 | 6/2002 | Soudant et al. |
| 2004/0202736 | A1 | 10/2004 | Munoz et al. |

FOREIGN PATENT DOCUMENTS

| | | |
|---|---|---|
| EP | 1 002 526 A1 | 5/2000 |
| JP | 63300071 | 11/1988 |
| JP | 02247196 A | 10/1990 |
| JP | 06128143 A | 5/1994 |
| JP | 07017845 A | 1/1995 |
| JP | 09279901 | 9/1997 |
| KR | 180688 | 3/1999 |
| KR | 190992 | 6/1999 |
| KR | 190993 | 6/1999 |
| WO | WO 99/55303 | 11/1999 |

OTHER PUBLICATIONS

Edenharder et al., Mut. Res., 1985, 341 :303-318. Modifying Actions of Solvent Extracts from Fruit & Vegetable Residues on 2-Amino-3-methylimidazo[4, 5-f] quinoline and 2-amino-3, 4-dimethylimodazo [4,5-f]quinoxalineinduced mutagenesis in *S. typhimurium* TA98.
http:home.planet.nl/skok/techniques/hplc/eluotropic.html. Equal Solvent Strengths. Jun. 6, 2004.
Pavia, D.L. et al., Introduction to Organic Laboratory Techniques, Third edition, 1988. Sauders College Publishing, U.S.A. Chapter Technique 5 : Extraction, The Separatory Funnel, Drying Agents, pp. 541-550.
Green, J. The Herbal Medicine-Maker's Handbook : A Home Manual, 2000. The Crossing Press, U.S.A. Chapter 5 : The Extraction Process, pp. 74-77, Chapter 6 : Solvents, pp. 80-98.

*Primary Examiner*—Michele Flood
(74) *Attorney, Agent, or Firm*—Brinks Hofer Gilson & Lione

(57) ABSTRACT

A skin whitening composition includes an extract of black cohosh obtained by sequentially exposing the black cohosh to two or more solvents of varying solvent strengths. The root of the black cohosh can be separately used to obtain the extract. The composition can be topically applied to the human skin and can further include one or more cosmetically acceptable ingredients. A method of suppressing melanogenesis includes topically applying to the skin a composition comprising an extract of black cohosh obtained by sequentially exposing the black cohosh to two or more solvents of varying solvent strength.

20 Claims, No Drawings

SKIN WHITENING COMPOSITIONS CONTAINING BLACK COHOSH EXTRACT

CROSS-REFERENCE TO RELATED APPLICATIONS

This application is a divisional of U.S. patent application Ser. No. 10/417,914 filed on Apr. 16, 2003, now U.S. Pat. No. 7,060,304. The disclosure of the above application is incorporated herein by reference.

BACKGROUND OF THE INVENTION

The present invention relates to skin whitening compositions that contain an extract of black cohosh. The extract can be obtained by exposing the black cohosh, or a portion thereof, to a single solvent or by sequentially exposing the black cohosh to two or more solvents of varying solvent strengths. The compositions are suitable for external use through topical application. The present invention further relates to the cosmetic use of such compositions, and a method of suppressing melanogenesis.

Skin color is primarily determined by the amount of melanin in the skin. Melanin is a brown-black pigment present in the skin. Due to the dark color of the pigment, lower amounts of melanin result in lighter skin color while higher amounts result in darker skin color. Melanin is formed by the oxidation of the amino acid tyrosine to dihydroxyphenalanine in melanocytes. This reaction is catalyzed by the enzyme tyrosinase.

As a result of this pivotal role of tyrosinase in melanin formation, efforts to develop effective skin whitening compositions have focused on agents that inhibit the function and activity of tyrosinase. For example, compositions have been proposed that include a variety of known tyrosinase inhibitors, such as hydroquinone, vitamin C and its derivatives, kojic acid, arbutin, glutathione, cysteine, and mulberry extract, among others. Compositions including these agents achieve a skin whitening effect through inhibition of the catalysis of the tyrosine oxidation reaction by tyrosinase.

The present inventors have discovered that certain extracts of black cohosh effectively suppress the formation of melanin, melanogenesis, despite the fact that the extracts show little to no inhibition of tyrosinase activity. This result is surprising and unexpected considering the pivotal role of tyrosinase in melanogenesis and the focus of development efforts in the art to inhibit this enzyme.

BRIEF SUMMARY OF THE INVENTION

The present invention provides skin whitening compositions suitable for external use through topical application. The compositions according to the present invention comprise an extract of black cohosh. The extract can be obtained by exposing the black cohosh, or a portion thereof, to a single solvent, such as $CO_2$ using supercritical fluid extraction. The extract can also be obtained by sequentially exposing the black cohosh, or a portion thereof, to two or more solvents of varying solvent strength. In a desirable embodiment, the extract is obtained by sequentially exposing a portion of the black cohosh plant to two or more solvents in increasing order of solvent strength.

In the compositions of the present invention, the extract desirably comprises between about 0.10 and about 20% (wt/wt) of the total composition. Particularly desirably, the extract comprises between about 0.25 and about 15% (wt/wt) of the total composition. Still more desirable, the extract comprises between about 0.50 and 10% (wt/wt) of the total composition.

The extract can be obtained from a portion of a black cohosh plant. The root portion is a desirable portion of the black cohosh plant for use in compositions according to the present invention.

The compositions according to the present invention can further comprise a variety of cosmetically acceptable ingredients. Furthermore, the compositions can be in the form of a preparation that facilitates topical application, such as a cream, ointment, foam, lotion, plaster, and emulsion.

The compositions of the present invention can be used cosmetically to effect skin whitening. Accordingly, the present invention also includes the cosmetic use of the compositions.

The present invention also includes a method of suppressing melanogenesis that comprises topically applying to the skin a composition according to the present invention.

DETAILED DESCRIPTION OF THE INVENTION

While the invention is defined by the claims below, additional understanding of the invention can be obtained by reviewing the following detailed description.

The present invention provides skin whitening compositions that comprise an extract of black cohosh. The black cohosh genus contains numerous species, and any suitable black cohosh plant within the black cohosh genus can be used in the compositions according to the present invention. The present inventors have discovered that *Cimicifuga racemosa* L. provides extracts that are particularly effective in skin whitening compositions.

The black cohosh used in the compositions can be one or more portions of the black cohosh plant. The root portion is a desirable portion of the black cohosh plant. As used herein, the term 'root' means any part of the black cohosh plant that is below the ground during the planted portion of the black cohosh plant lifecycle. Thus, the root is any sub-aerial component of the plant.

The black cohosh plant can be prepared for extraction by subdividing the plant into small pieces. The small pieces are ground into a powder form, such as by mechanical disruption in a blender or other similar means. If less than the whole plant is being used, the desired portions are first isolated from the remaining portions of the plant and then subdivided into small pieces and ground into a powder form. Alternatively, powdered black cohosh can be obtained from a commercial source, such as Costec of Lake Zurich, Ill.

The extract for use in the composition is obtained by exposing a black cohosh, or a portion thereof, to one or more solvents. Desirably, the extract is obtained by sequentially exposing a black cohosh, or a portion thereof, to two or more solvents of varying solvent strength. As used herein, the term 'sequentially exposing' means exposing the black cohosh to a first solvent, removing the residue, and exposing the residue to a second solvent. The term can include any number of these steps, and therefore can include any number of solvents. The number of extraction steps included will depend on various factors, including the melanogenesis inhibiting ability of the various fractions obtained at each step. Example 1 provides a suitable experimental method for determining the ability of a particular fraction to inhibit melanogenesis. As used herein, the term "solvent strength" refers to the eluotropic strength of a solvent on silica, which is a quantitative representation of the rate at which a solvent elutes a compound from silica. Solvent strength is described in the HPLC Solvent Guide, by Paul C. Sadek (John Wiley and Sons, 1996, ISBN 0-471-11855-9), which is hereby incorporated by reference for this purpose.

As used herein, the term "varying solvent strength(s)" refers to solvents with different eluotropic strengths with silica, represented by $\epsilon°$ (SiOH). Based on the eluotropic scale with SiOH, solvents can roughly be grouped into the following categories: low solvent strength (0.00-0.35 $\epsilon°$ (SiOH)); medium solvent strength (0.36-0.55 $\epsilon°$ (SiOH)); high solvent strength (0.56-0.75 $\epsilon°$ (SiOH)); and very high solvent strength (>0.76 $\epsilon°$ (SiOH)).

Desirably, the extract is obtained by exposing the black cohosh to two or more solvents of varying solvent strengths. When two or more solvents are used, it is desirable to arrange the solvents in increasing order of solvent strength. Thus, the black cohosh is desirably sequentially exposed to two or more solvents of varying solvent strength, in order of increased solvent strength. For example, the black cohosh is desirably exposed to low solvent strength, medium solvent strength, and high solvent strength solvents. Also, a very high solvent strength solvent can be added.

If a single solvent is utilized, it is desirable that the single solvent include components of varying solvent strengths. For example, it is desirable that the single solvent include components having low, medium, and high solvent strengths. A suitable solvent is $CO_2$ using supercritical fluid extraction techniques. In this embodiment, $CO_2$ is compressed to its critical point, desirably through pressure and temperature. The density of the $CO_2$ can be further modified by temperature and/or pressure alterations to produce liquid $CO_2$ samples of differing densities, which display a wide-range of solvent strengths. These samples are then used to extract the black cohosh. The use of $CO_2$ and supercritical fluid extraction techniques is desirous because it allows for a single solvent, and the $CO_2$ evaporates after extraction eliminating separation steps. Surfactants, such as anionic, cationic, amphoteric, and nonionic surfactants can also be used as solvents.

A variety of solvents can be used to obtain extracts of black cohosh for use in the compositions according to the present invention. The solvent(s) chosen need only be able to produce an extract that possesses the desired suppression of melanogenesis. Examples of suitable low solvent strength solvents (i.e., $\epsilon°$ (SiOH) 0.00-0.35) include low aliphatic hydrocarbons (e.g., hexane, mineral oil), aliphatic alcohols (e.g., dodecanol), aromatic hydrocarbons (e.g., toluene), chlorinated hydrocarbons (e.g., chloroform, methylene chloride), aliphatic esters (e.g., vegetable oils, isopropyl myristate), aliphatic ethers (e.g., dicaprylyl ether), and silicone fluids (e.g., methicone, cyclomethicone, dimethicone).

Examples of suitable medium solvent strength solvents (i.e., $\epsilon°$ (SiOH) 0.36-0.55) include medium light ketones (e.g., acetone, methyl ethyl ketone), light ethers (e.g., ethyl ether, tetrahydrafuran, dioxane), light esters (e.g., ethyl acetate), alkylene glycols (e.g., butylenes, propylene), polyols (e.g., sorbitol, glycerin), glycol ethers (e.g., dimethyl isosorbide, ethoxydiglycol), ethoxylates (e.g., PEG-8), and propoxylates (e.g., PPG-9).

Examples of suitable high solvent strength solvents include high light alcohols, such as methanol, ethanol, and isopropanol.

Examples of suitable very high strength solvents (i.e., $\epsilon°$ (SiOH) >0.76) include water and other aqueous based solvents and solvent blends, such as hydroethanol.

As indicated above, it is particularly desirable to order the solvents by increasing degree of solvent strength.

As used herein, the term 'hydroethanol' refers to a mixture of ethanol and water. Any suitable ratio of ethanol to water can be used to prepare the hydroethanol. A desirable mixture comprises one part ethanol and one part water.

As indicated above, the extract is desirably obtained by sequentially exposing black cohosh, or a portion thereof, to two or more solvents of varying solvent strength. The following procedure is suitable for obtaining extracts for use in accordance with the present invention. A powdered plant material, obtained as described above, is exposed to a first solvent. This preparation is sonicated to facilitate extraction, and then centrifuged to separate the residue and an extract. The first extract is removed and the residue is dried by desiccation. Next, the residue is exposed to a second solvent. Again, this preparation is sonicated and centrifuged. The second extract is removed, and the remaining residue is dried by desiccation. The residue is further extracted by sequential exposure to further solvents. For each of these steps, the extract procedure is identical to that described for the first two solvents.

If a single solvent is used, the powdered material, obtained as described above, can be exposed to the solvent, and separated from the residue following an extraction, which may include a step for facilitating extraction, such as sonication.

Following this procedure, four extracts are obtained, and can be individually evaluated for the ability to inhibit melanogenesis. Example 2 provides a suitable experimental method for determining the ability of an extract to inhibit melanogenesis. Any of these extracts can be utilized in the skin whitening compositions according to the present invention.

The amount of extract present in a skin whitening composition will depend upon several factors, including the desired level of suppression of melanogenesis, the capacity of a particular preparation for a particular extract, and other factors. Desirably, the extract comprises between about 0.10 and about 20% (wt/wt) of the total composition. Particularly desirably, the extract comprises between about 0.25 and about 15% (wt/wt) of the total composition. Still more desirable, the extract comprises between about 0.50 and 10% (wt/wt) of the total composition.

The present invention also provides preparations that include the skin whitening compositions. The compositions may be prepared in various forms, and are desirably prepared in a form that facilitates topical application. Accordingly, suitable forms of preparation include a cream, ointment, foam, lotion, plaster, gel, and emulsion.

In each preparation, various known conventional cosmetic ingredients may be incorporated. Any additional ingredients used in the compositions must not be irritating, and should not detrimentally effect the desired suppression of melanogenesis. One example of an additional ingredient that might be included is a conventional cosmetically acceptable vehicle. A variety of vehicles can be used. Examples of suitable vehicles include those that maintain the extract in a soluble and homogenous state in a liquid form. Specific examples of desirable vehicles include propylene glycol and butylene glycol. Additional examples of other suitable cosmetically acceptable ingredients include alcohols, fats and oils, surfactants, fatty acids, silicone oils, humectants, moisturizers, viscosity modifiers, emulsifiers, stabilizers, coloring agents, and perfumes.

The compositions of the present invention are particularly well suited for topical application and for use as skin whitening agents. Accordingly, the present invention also includes the cosmetic use of the compositions according to the present invention. Specifically, the present invention includes the cosmetic use of a composition comprising an extract of black cohosh obtained by sequentially exposing the black cohosh to two or more solvents of varying polarity. Further, the invention specifically includes the cosmetic use of a composition comprising a low solvent strength solvent extract of a portion of black cohosh. Desirably, the low solvent strength solvent extract comprises an extract of the root portion of a black cohosh.

The present invention also provides a method of suppressing melanogenesis. The method comprises topically applying to the skin a composition that comprises an extract of black cohosh. Desirably, the extract is either a low solvent strength solvent extract of a root of a black cohosh. Also desirable, the extract can be obtained by sequentially exposing the black cohosh to two or more solvents of varying solvent strengths. Particularly desirable, the extract is obtained by sequentially exposing the black cohosh to two or more solvents of varying solvent strength in order of increased solvent strength.

In the method, the frequency of topical applications will depend on several factors, including the desired level of suppression of melanogenesis. The compositions of the present invention can desirably be applied to the skin twice daily, and are particularly desirably applied once in the morning and once in the evening. The amount of the composition used in each application will also depend on several factors, including the desired level of suppression of melanogenesis and the content of the extract in the composition.

The present invention also provides a method of determining an acceptable extract of a plant for use in compositions and methods for suppressing melanogenesis. The method comprises sequentially exposing the plant, or a portion thereof, to two or more solvents of varying solvent strength, isolating at least two separate extracts, and individually evaluating each extract for the ability to suppress melanogenesis.

EXAMPLES

Example 1

Suppression of Melanogenesis

A modified version of a known assay was utilized to determine the ability of various extracts to suppress melanogenesis in vitro (see Dooley, T. P., et al., *Skin Pharmacol.* 7:188-200 (1994), which is hereby incorporated in its entirety for the purpose of determination of the ability to suppress melanogenesis). Briefly, mouse derived immortalized melanocyte cells (M3, ATCC, Menasis, Va.) were grown in F12K media (Invitrogen, Carlsban, Calif.) supplemented with 10% fetal bovine serum, 100 nM 12-0-tetradecanoylphorbol-13 acetate and 1 nM cholera toxin. The cells were plated on six well microtitre plates 24 hours prior to initial treatment. The cells were treated with various test samples by adding an aliquot of the test sample to the culture medium. Treatments were applied at 1, 3, and 5 days. On day 6, melanin was extracted from the culture medium using 1N NaOH. Relative quantity of extracted melanin was determined by optical density using spectrophotometer measurement at 405 nm. Also, coloration of the cells was visually determined by counting the extent of melanized cells present in a microscopic field viewed under 200× magnification.

Table 1 provides results for assays in which the ability of various extracts to suppress melanogenesis was determined, including positive and negative controls. As the data clearly indicate, all evaluated extracts were able to suppress melanogenesis despite an inability to inhibit the activity of tyrosinase (data not shown).

TABLE 1

|  | Fraction | Treatment Dose | % Control Melanin | Visual |
| --- | --- | --- | --- | --- |
| -Control |  | 0 | 100% | ++++ |
| Ascorbic Acid |  | 0.100% | 51% | ++ |
| Black cohosh Root | Hexane | 0.005% | 54% | ++ |
|  | Acetone | 0.020% | 45% | +++ |
|  | Methanol | 0.010% | 36% | +++ |
|  | H/EA | 0.065% | 91% | +++ |
|  | Total | 0.100% | 68% | ++ |

The invention claimed is:

1. A method of suppressing melanogenesis, comprising topically applying to skin an effective amount of a composition comprising an extract of black cohosh (*Cimicifuga racemosa*) obtained by exposing a root of the black cohosh to two or more solvents of varying solvent strengths, where the solvents are selected from the group consisting of a solvent with low solvent strength (0.00-0.35 $\epsilon°$ (SiOH)), a solvent with medium solvent strength (0.36-0.55 $\epsilon°$ (SiOH)), a solvent with high solvent strength (0.56-0.75 $\epsilon°$ (SiOH)), and a solvent with very high solvent strength (>0.76 $\epsilon°$ (SiOH)).

2. The method of claim 1 wherein the black cohosh comprises *Cimicifuga racemosa* L.

3. The method of claim 1 wherein the extract of black cohosh is obtained by sequentially exposing the root of the black cohosh to two or more solvents of varying solvent strengths.

4. The method of claim 3 wherein the two or more solvents are in order of increasing solvent strength.

5. The method of claim 1 wherein the composition comprises between about 0.1% and about 20% extract of black cohosh in the total composition.

6. The method of claim 1 wherein the black cohosh is exposed to a solvent with low solvent strength (0.00-0.35 $\epsilon°$ (SiOH)), a solvent with medium solvent strength (0.36-0.55 $\epsilon°$ (SiOH)), and a solvent with high solvent strength (0.56-0.75 $\epsilon°$ (SiOH)).

7. The method of claim 6 wherein the solvent with low solvent strength is selected from the group consisting of hexane, mineral oil, aliphatic alcohols, aromatic hydrocarbons, chlorinated hydrocarbons, aliphatic esters, aliphatic ethers, and silicone fluids.

8. The method of claim 6 wherein the solvent with medium solvent strength is selected from the group consisting of acetone, methyl ethyl ketone, ethyl ether, tetrahydrafuran, dioxane, ethyl acetate, alkylene glycols, polyols, glycol ethers, ethoxylates, and propoxylates.

9. The method of claim 6 wherein the solvent with high solvent strength comprises a high light alcohol.

10. The method of claim 6 further comprising exposing the black cohosh to a solvent with very high solvent strength (>0.76 $\epsilon°$ (SiOH)).

11. The method of claim 10 wherein the solvent with very high solvent strength comprises water, an aqueous-based solvent, or an aqueous-based solvent blend.

12. The method of claim 11 wherein the solvent with very high solvent strength comprises hydroethanol.

13. The method of claim 12 wherein the hydroethanol comprises one part ethanol and one part water.

14. The method of claim 1 wherein at least one solvent is a surfactant.

15. A method of suppressing melanogenesis, comprising topically applying to the skin a composition comprising an extract of black cohosh (*Cimicifuga racemosa*) obtained by exposing a root of the black cohosh to:
- a. a solvent with low solvent strength (0.00-0.35 $\epsilon°$ (SiOH)) comprising a low aliphatic hydrocarbon selected from the group consisting of hexane and mineral oil;
- b. a solvent with medium solvent strength (0.36-0.55 $\epsilon°$ (SiOH)); and
- c. a solvent with high solvent strength (0.56-0.75 $\epsilon°$ (SiOH)).

16. The method of claim 15 further comprising exposing the root of the black cohosh to hydroethanol.

17. A method of suppressing melanogenesis, comprising topically applying to the skin a composition comprising an extract of black cohosh (*Cimicifuga racemosa*) obtained by exposing a root of the black cohosh to two or more solvents of varying solvent strengths, wherein the two or more solvents are in order of increasing solvent strength, wherein a first solvent comprises a low aliphatic hydrocarbon selected from the group consisting of hexane and mineral oil, and wherein a second solvent comprises a solvent selected from the group consisting of a solvent with low solvent strength (0.00-0.35 $\epsilon°$ (SiOH)), a solvent with medium solvent strength (0.36-0.55 $\epsilon°$ (SiOH)), a solvent with high solvent strength (0.56-0.75 $\epsilon°$ (SiOH)), and a solvent with very high solvent strength (>0.76 $\epsilon°$ (SiOH)).

18. The method of claim 4 wherein a first solvent comprises a low aliphatic hydrocarbon selected from the group consisting of hexane and mineral oil.

19. The method of claim 1 wherein the extract exhibits substantially no inhibition of tyrosinase.

20. The method of claim 17 wherein the extract exhibits substantially no inhibition of tyrosinase.

* * * * *